(12) United States Patent
Justis et al.

(10) Patent No.: US 8,057,519 B2
(45) Date of Patent: Nov. 15, 2011

(54) MULTI-AXIAL SCREW ASSEMBLY

(75) Inventors: Jeff R Justis, Germantown, TN (US);
Fred J. Molz, IV, Birmingham, AL (US); James M Mirda, Cordova, TN (US); Rodney R Ballard, Lakeland, TN (US); Robert A Farris, Cordova, TN (US); Jason M May, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 913 days.

(21) Appl. No.: 12/038,572

(22) Filed: Feb. 27, 2008

(65) Prior Publication Data
US 2008/0147121 A1   Jun. 19, 2008

Related U.S. Application Data

(63) Continuation-in-part of application No. 11/493,447, filed on Jul. 26, 2006, now Pat. No. 7,833,252, which is a continuation-in-part of application No. 11/341,188, filed on Jan. 27, 2006, now Pat. No. 7,722,652.

(51) Int. Cl.
*A61B 17/70* (2006.01)
(52) U.S. Cl. .................. 606/270; 606/266; 606/306
(58) Field of Classification Search .......... 606/264–275, 606/300–308
See application file for complete search history.

(56) References Cited

U.S. PATENT DOCUMENTS

| | | |
|---|---|---|
| 4,304,011 A | 12/1981 | Whelan, II |
| 4,946,458 A | 8/1990 | Harms et al. |
| 5,084,048 A | 1/1992 | Jacob et al. |
| 5,190,543 A | 3/1993 | Schlapfer |
| 5,443,467 A | 8/1995 | Biedermann et al. |
| 5,474,555 A | 12/1995 | Puno et al. |
| 5,480,041 A | 1/1996 | Turner |
| 5,549,608 A | 8/1996 | Errico et al. |
| 5,591,166 A | 1/1997 | Bernhardt et al. |
| 5,669,911 A | 9/1997 | Errico et al. |
| 5,728,098 A | 3/1998 | Sherman et al. |
| 5,733,285 A | 3/1998 | Errico et al. |
| 5,797,911 A | 8/1998 | Sherman et al. |
| 5,810,819 A | 9/1998 | Errico et al. |
| 5,817,094 A | 10/1998 | Errico et al. |
| 5,863,293 A | 1/1999 | Richelsoph |
| 5,882,350 A | 3/1999 | Ralph et al. |
| 5,885,286 A | 3/1999 | Sherman et al. |
| 5,888,204 A | 3/1999 | Ralph et al. |
| 5,891,145 A | 4/1999 | Morrison et al. |
| 5,954,725 A | 9/1999 | Sherman et al. |
| 5,989,254 A | 11/1999 | Katz |
| 6,063,090 A | 5/2000 | Schlapfer |
| 6,074,391 A | 6/2000 | Metz-Stavenhagen et al. |
| 6,082,923 A | 7/2000 | Maughan |

(Continued)

FOREIGN PATENT DOCUMENTS
EP   1570794 A1   9/2005
(Continued)

OTHER PUBLICATIONS

Orbitform Group, LLC, "What is Orbit Forming." *Orbitform: Manufacturer of Orbital Forming, Fastening, Riveting, Assembly, Heat Sinking Systems and...*, Jun. 1, 2007, 2 pages. http://www.orbitform.com/riveting/what_is_orbital_forming.htm.

(Continued)

*Primary Examiner* — Eduardo C Robert
*Assistant Examiner* — Ellen C Hammond (57) ABSTRACT

The present application is directed to multi-axial screw assemblies to connect a longitudinal member to a vertebral member. In one embodiment, the multi-axial screw assembly includes a screw comprising a threaded shank and an enlarged head. The assembly may also include a body with an upper channel sized to receive the longitudinal member, a lower chamber to receive the head. The body is constructed to maintain the head in the lower chamber.

14 Claims, 9 Drawing Sheets

U.S. PATENT DOCUMENTS

| | | |
|---|---|---|
| 6,132,434 A | 10/2000 | Sherman et al. |
| 6,146,421 A | 11/2000 | Gordon et al. |
| 6,248,105 B1 | 6/2001 | Schlapfer et al. |
| 6,258,089 B1 | 7/2001 | Campbell et al. |
| 6,261,287 B1 | 7/2001 | Metz-Stavenhagen |
| 6,280,442 B1 | 8/2001 | Barker et al. |
| 6,287,311 B1 | 9/2001 | Sherman et al. |
| 6,290,703 B1 | 9/2001 | Ganem |
| RE37,665 E | 4/2002 | Ralph et al. |
| 6,368,321 B1 | 4/2002 | Jackson |
| 6,440,137 B1 | 8/2002 | Horvath et al. |
| 6,454,773 B1 | 9/2002 | Sherman et al. |
| 6,537,276 B2 | 3/2003 | Metz-Stavenhagen |
| 6,554,834 B1 | 4/2003 | Crozet et al. |
| 6,605,090 B1 | 8/2003 | Trieu et al. |
| 6,626,907 B2 | 9/2003 | Campbell et al. |
| 6,626,908 B2 | 9/2003 | Cooper et al. |
| 6,660,004 B2 | 12/2003 | Barker et al. |
| 6,716,214 B1 | 4/2004 | Jackson |
| 6,733,502 B2 | 5/2004 | Altarac et al. |
| 6,736,820 B2 | 5/2004 | Biedermann et al. |
| 6,749,361 B2 | 6/2004 | Hermann et al. |
| 6,793,658 B2 | 9/2004 | LeHuec et al. |
| 6,869,433 B2 | 3/2005 | Glascott |
| 6,918,911 B2 | 7/2005 | Biedermann et al. |
| 6,945,972 B2 | 9/2005 | Frigg et al. |
| 6,964,666 B2 | 11/2005 | Jackson |
| 6,974,460 B2 | 12/2005 | Carbone et al. |
| 6,974,461 B1 | 12/2005 | Wolter |
| 6,991,632 B2 | 1/2006 | Ritland |
| 7,022,122 B2 | 4/2006 | Amrein et al. |
| 7,060,067 B2 | 6/2006 | Needham et al. |
| 7,066,937 B2 | 6/2006 | Shluzas |
| 7,081,116 B1 | 7/2006 | Carly |
| 7,081,117 B2 | 7/2006 | Bono et al. |
| 7,087,057 B2 | 8/2006 | Konieczynski et al. |
| 7,090,674 B2 | 8/2006 | Doubler et al. |
| 7,121,755 B2 | 10/2006 | Schlapfer et al. |
| 7,128,743 B2 | 10/2006 | Metz-Stavenhagen |
| 7,141,051 B2 | 11/2006 | Janowski et al. |
| 7,144,396 B2 | 12/2006 | Shluzas |
| 7,163,539 B2 | 1/2007 | Abdelgany et al. |
| 7,166,109 B2 | 1/2007 | Biedermann et al. |
| 7,179,261 B2 | 2/2007 | Sicvol et al. |
| 7,186,255 B2 | 3/2007 | Baynham et al. |
| 7,195,632 B2 | 3/2007 | Biedermann et al. |
| 7,214,227 B2 | 5/2007 | Colleran et al. |
| 7,223,268 B2 | 5/2007 | Biedermann |
| 7,699,876 B2 | 4/2010 | Barry et al. |
| 2002/0138076 A1 | 9/2002 | Biedermann et al. |
| 2003/0045879 A1 | 3/2003 | Minfelde et al. |
| 2004/0049272 A1 | 3/2004 | Reiley |
| 2004/0102781 A1 | 5/2004 | Jeon |
| 2004/0116929 A1 | 6/2004 | Barker et al. |
| 2004/0176766 A1 | 9/2004 | Shluzas |
| 2004/0181224 A1 | 9/2004 | Biedermann et al. |
| 2004/0186473 A1 | 9/2004 | Cournoyer et al. |
| 2004/0225289 A1 | 11/2004 | Biedermann et al. |
| 2004/0249380 A1 | 12/2004 | Glascott |
| 2004/0260284 A1 | 12/2004 | Parker |
| 2004/0267264 A1* | 12/2004 | Konieczynski et al. ......... 606/73 |
| 2005/0033431 A1 | 2/2005 | Gordon et al. |
| 2005/0033432 A1 | 2/2005 | Gordon et al. |
| 2005/0033439 A1 | 2/2005 | Gordon et al. |
| 2005/0049588 A1 | 3/2005 | Jackson |
| 2005/0049589 A1 | 3/2005 | Jackson |
| 2005/0187548 A1 | 8/2005 | Butler et al. |
| 2005/0192571 A1 | 9/2005 | Abdelgany |
| 2005/0203516 A1 | 9/2005 | Biedermann et al. |
| 2005/0209698 A1 | 9/2005 | Gordon et al. |
| 2005/0228385 A1 | 10/2005 | Iott et al. |
| 2005/0267472 A1 | 12/2005 | Biedermann et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0277919 A1* | 12/2005 | Slivka et al. ................ 606/61 |
| 2005/0277925 A1* | 12/2005 | Mujwid ................ 606/61 |
| 2005/0277928 A1 | 12/2005 | Boschert et al. |
| 2005/0278026 A1 | 12/2005 | Gordon et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2005/0288668 A1 | 12/2005 | Brinkhaus |
| 2006/0036242 A1 | 2/2006 | Nilsson et al. |
| 2006/0084979 A1 | 4/2006 | Jackson |
| 2006/0161152 A1 | 7/2006 | Ensign et al. |
| 2006/0173454 A1 | 8/2006 | Spitler et al. |
| 2006/0195098 A1 | 8/2006 | Schumacher |
| 2006/0200128 A1 | 9/2006 | Mueller |
| 2006/0200131 A1 | 9/2006 | Chao et al. |
| 2006/0200133 A1 | 9/2006 | Jackson |
| 2006/0200136 A1 | 9/2006 | Jackson |
| 2006/0217713 A1 | 9/2006 | Serhan et al. |
| 2006/0217714 A1 | 9/2006 | Serhan et al. |
| 2006/0217715 A1 | 9/2006 | Serhan et al. |
| 2006/0217716 A1 | 9/2006 | Baker et al. |
| 2006/0229616 A1 | 10/2006 | Albert et al. |
| 2006/0235385 A1 | 10/2006 | Whipple |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241599 A1 | 10/2006 | Konieczynski et al. |
| 2006/0241600 A1 | 10/2006 | Ensign et al. |
| 2006/0241603 A1 | 10/2006 | Jackson |
| 2006/0241769 A1 | 10/2006 | Gordon et al. |
| 2006/0241771 A1 | 10/2006 | Gordon et al. |
| 2006/0247631 A1 | 11/2006 | Ahn et al. |
| 2006/0247636 A1 | 11/2006 | Yuan et al. |
| 2006/0264933 A1 | 11/2006 | Baker et al. |
| 2006/0271047 A1 | 11/2006 | Jackson |
| 2006/0271053 A1 | 11/2006 | Schlapfer et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0293659 A1 | 12/2006 | Alvarez |
| 2006/0293664 A1 | 12/2006 | Schumacher |
| 2006/0293665 A1 | 12/2006 | Shluzas |
| 2006/0293666 A1 | 12/2006 | Matthis et al. |
| 2007/0016198 A1 | 1/2007 | Boehm et al. |
| 2007/0016199 A1 | 1/2007 | Boehm et al. |
| 2007/0016200 A1 | 1/2007 | Jackson |
| 2007/0021750 A1 | 1/2007 | Shluzas et al. |
| 2007/0043355 A1 | 2/2007 | Bette et al. |
| 2007/0043357 A1 | 2/2007 | Kirschman |
| 2007/0043358 A1 | 2/2007 | Molz et al. |
| 2007/0043364 A1 | 2/2007 | Cawley et al. |
| 2007/0049933 A1 | 3/2007 | Ahn et al. |
| 2007/0055235 A1 | 3/2007 | Janowski et al. |
| 2007/0055238 A1 | 3/2007 | Biedermann et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0073291 A1 | 3/2007 | Cordaro et al. |
| 2007/0078460 A1 | 4/2007 | Frigg et al. |
| 2007/0083199 A1 | 4/2007 | Baccelli |
| 2007/0088357 A1 | 4/2007 | Johnson et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093821 A1 | 4/2007 | Freudiger |
| 2007/0093826 A1 | 4/2007 | Hawkes et al. |
| 2007/0093827 A1 | 4/2007 | Warnick |
| 2007/0093829 A1 | 4/2007 | Abdou |
| 2007/0093831 A1 | 4/2007 | Abdelgany et al. |
| 2007/0093832 A1 | 4/2007 | Abdelgany |
| 2007/0100341 A1 | 5/2007 | Reglos et al. |
| 2007/0106383 A1 | 5/2007 | Abdou |
| 2007/0118117 A1 | 5/2007 | Altarac et al. |
| 2007/0118118 A1 | 5/2007 | Kwak et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123867 A1 | 5/2007 | Kirschman |

| | | | |
|---|---|---|---|
| 2007/0123870 A1 | 5/2007 | Jeon et al. | |
| 2007/0191839 A1 | 8/2007 | Justis et al. | |
| 2007/0233078 A1 | 10/2007 | Justis et al. | |

FOREIGN PATENT DOCUMENTS

| | | | |
|---|---|---|---|
| WO | WO 2005/004699 A2 | 1/2005 | |
| WO | WO 2005/016194 A2 | 2/2005 | |
| WO | 2007130835 A2 | 11/2007 | |

OTHER PUBLICATIONS

Orbitform Group, LLC, "What is Rollerforming." *Orbitform: Manufacturer of Orbital Forming, Fastening, Riveting, Assembly, Heat Sinking Systems and...*, Jun. 1, 2007, 2 pages. http://www.orbitform.com/products/orbitform/Rollerform_Heads.htm.

* cited by examiner

MULTI-AXIAL SCREW ASSEMBLY

This application is a continuation-in-part of U.S. patent application Ser. No. 11/493,447 filed Jul. 26, 2006 that itself is a continuation-in-part of U.S. patent application Ser. No. 11/341,188, filed Jan. 27, 2006.

BACKGROUND

Longitudinal members, such as spinal rods, are often used in the surgical treatment of spinal disorders such as degenerative disc disease, disc herniations, scoliosis or other curvature abnormalities, and fractures. Treatment of these spinal disorders may use different types of surgical treatments. In some cases, spinal fusion is indicated to inhibit relative motion between vertebral members. In other cases, dynamic implants are used to preserve motion between vertebral members. For either type of surgical treatment, longitudinal members may be attached to the exterior of two or more vertebral members, whether it is at a posterior, anterior, or lateral side of the vertebral members. In other embodiments, longitudinal members are attached to the vertebral members without the use of dynamic implants or spinal fusion.

Longitudinal members may provide a stable, rigid column that encourages bones to fuse after spinal-fusion surgery. Further, the longitudinal members may redirect stresses over a wider area away from a damaged or defective region. Also, rigid longitudinal members may restore the spine to its proper alignment. In some cases, flexible longitudinal members may be appropriate. Flexible longitudinal members may provide other advantages, such as increasing loading on interbody constructs, decreasing stress transfer to adjacent vertebral members while bone-graft healing takes place, and generally balancing strength with flexibility.

SUMMARY

One embodiment of the present application is directed to multi-axial screw assemblies to connect a longitudinal member to a vertebral member. In one embodiment, the multi-axial screw assembly includes a screw comprising a threaded shank and an enlarged head. The assembly may also include a body with an upper channel sized to receive the longitudinal member, a lower chamber to receive the head. The body is constructed to maintain the head in the lower chamber.

DETAILED DESCRIPTION

Figure 1:
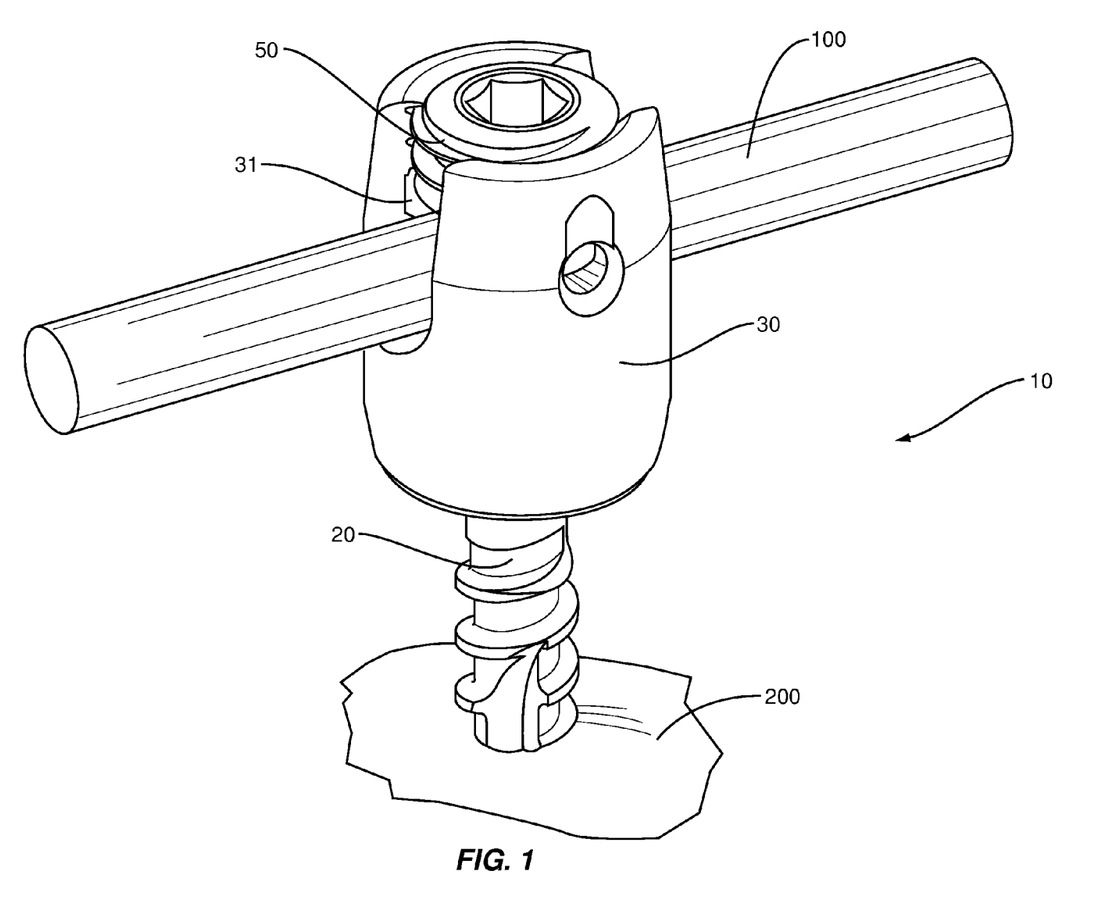
FIG. 1 is a perspective view of a multi-axial screw assembly and a longitudinal member according to one embodiment.

The present application is directed to multi-axial screw assemblies for attaching a longitudinal member to a vertebral member. FIG. 1 illustrates one embodiment of a screw assembly 10 that includes a screw 20 and a receiver 30. The screw 20 includes an elongated shape with a first end mounted within a vertebral member 200 and a second end extending outward above the vertebral member 200. The receiver 30 is deformed to operatively connect to the second end of the screw 20 and is movably connected to the screw 20 to accommodate the longitudinal member 100 positioned at various angular positions. The receiver 30 includes a channel 31 sized to receive the longitudinal member 100. A set screw 50 attaches to the receiver 30 to capture the longitudinal member 100 within the channel 31.

Figure 2:
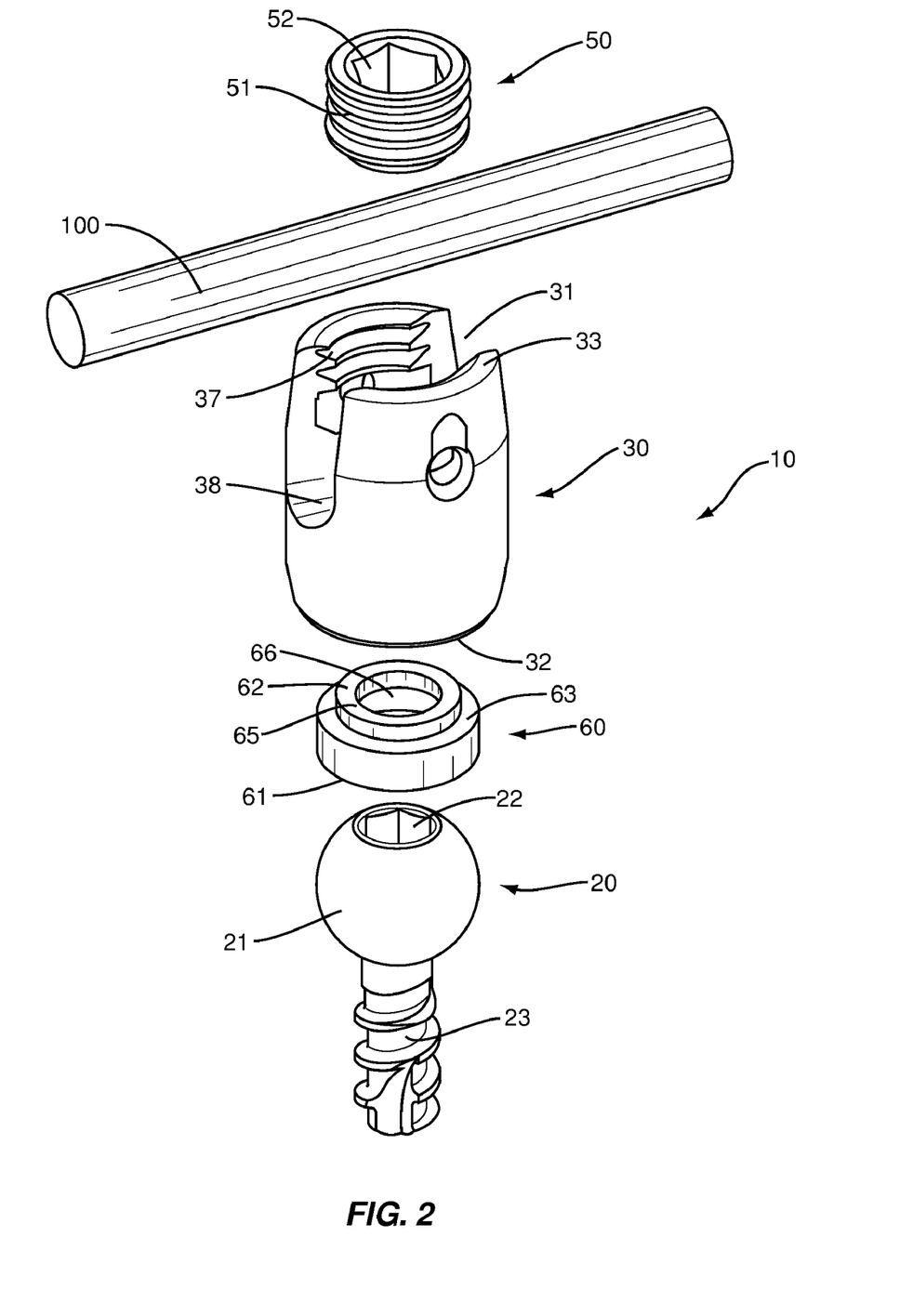
FIG. 2 is an exploded view of a multi-axial screw assembly and longitudinal member according to one embodiment.
Figure 3:
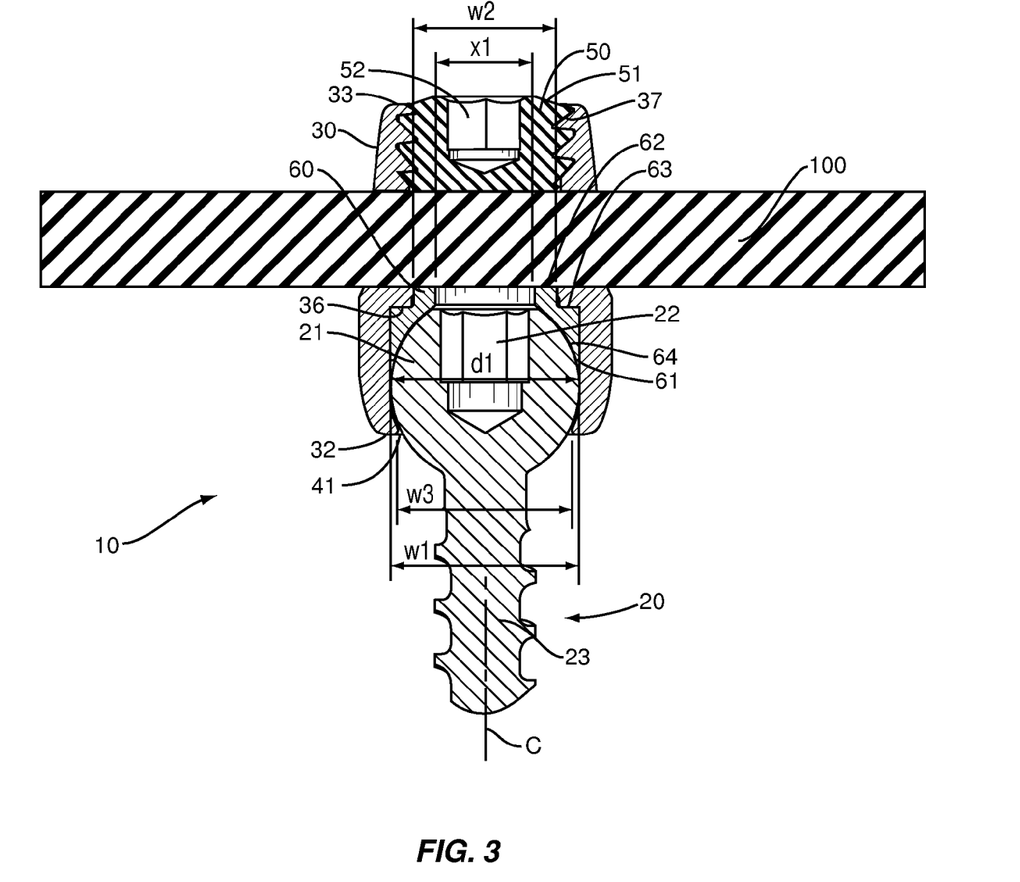
FIG. 3 is a section view of a multi-axial screw assembly and a longitudinal member according to one embodiment.

As illustrated in FIGS. 2 and 3, the screw 20 includes a head 21 positioned at an end of a shaft 23. The head 21 is substantially spherical and may include a driving feature 22 for insertion of the screw 20 into the vertebral member 200. Head 21 may also include other shapes, such as an elliptical shape. The embodiment illustrated includes a hex recess driving feature 22. Other types of driving features 22 may be appropriate, including for example, slotted, star, TORX, and cross-shaped features.

Head 21 includes a width d1 as illustrated in FIG. 3. The head 21 includes an exterior surface that is substantially smooth to facilitate pivoting movement with the receiver 30. The shaft 23 may include threads along an entirety or a limited portion to facilitate insertion into the vertebral member 200.

Receiver 30 provides a connection between the screw 20 and longitudinal member 100. Receiver 30 includes a first end 32 that faces towards the vertebral member 200, and a second end 33 that faces away. A chamber 34 is positioned between the first and second ends 32, 33 and is sized to receive the head 21. Chamber 34 includes a central section with a width w1 formed between interior sidewalls 35. In the embodiment illustrated, the width w1 is substantially equal to the width d1. In another embodiment, the width w1 may be larger than the width d1 for the head 21 to move laterally within the chamber 34. In another embodiment, the width w1 is smaller than the width d1.

The receiver 30 may be constructed as a unitary piece. As illustrated in FIG. 3, the receiver 30 defines an outer extent and also an inner wall of the chamber 34 at the vertical level where the head 21 is positioned. In one embodiment, the receiver 30 is circumferentially un-reinforced with the receiver 30 including adequate strength to maintain the screw 20.

An upper constriction 40 with a width w2 is formed in the receiver 30. The upper constriction 40 width w2 is smaller than the width w1 of the central section 49 of the chamber 34, and is smaller than the head width d1 thus preventing the head 21 from moving upward in the receiver 30 beyond this level. The upper constriction 40 may be formed by the receiver 30, by a crown 60 as explained below, or both. In the embodiments of FIGS. 2 and 3, the upper constriction 40 is formed by the receiver 30, and specifically a ledge 36 that extends inward from the sidewalls 35 at an upper section of the chamber 34 away from the first end 32.

Figure 6:
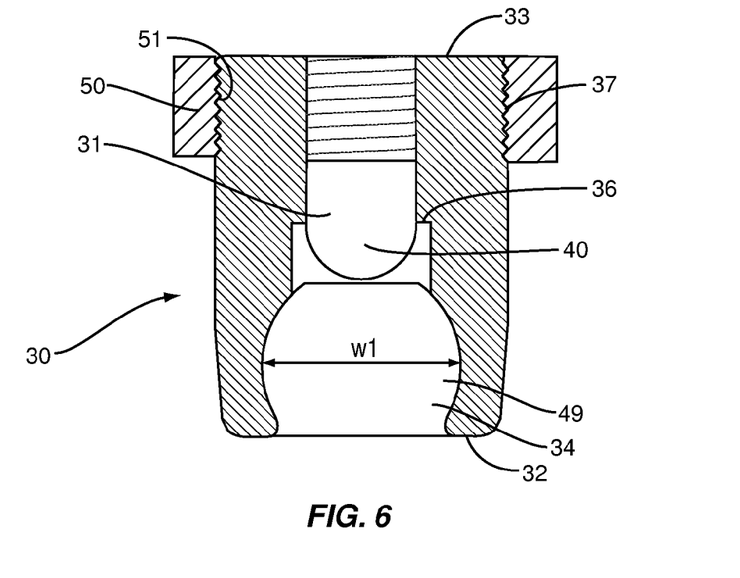
FIG. 6 is a section view of a receiver and a set screw according to one embodiment.

The second end 33 of the receiver 30 includes a channel 31 sized to receive the longitudinal member 100. Channel 31 terminates at a lower edge 38 that may include a curved shape to approximate the longitudinal member 100. Threads 37 may be positioned towards the second end 33 to engage with the set screw 50. In one embodiment as illustrated in FIG. 2, the threads 37 are positioned on the interior of the receiver 30 facing towards the channel 31. In another embodiment as illustrated in FIG. 6, the threads 37 are on the exterior of the receiver 30. An interior of the receiver 30 may be open between the first and second ends 32, 33. This open space provides for insertion of a driver through the receiver 30 to engage the driving feature 22 on the screw 20 and mount the screw 20 within the vertebral member 200.

Set screw 50 attaches to the receiver 30 and captures the longitudinal member 100 within the channel 31. As illustrated in FIG. 2, the set screw 50 may be sized to fit within the interior of the channel 31 and include exterior threads 51 that engage threads 37 on the receiver 30. A driving feature 52 may be positioned on a top side to receive a tool during engagement with the receiver 30. Driving feature 52 may be substantially the same or different than driving feature 22. FIG. 6 illustrates another embodiment with the set screw 50 mounted on an exterior of the receiver 30. Set screw 50 includes a central opening and is sized to extend around the second end 33. Threads 51 are positioned on an inner surface of the central opening to engage with the external threads 37 on the receiver 30. The set screw 50 and receiver 30 may be constructed for the top side of the set screw 50 to be flush with or recessed within the second end 33 when mounted with the receiver 30.

As illustrated in FIGS. 2 and 3, a crown 60 may be positioned within the receiver 30 between the screw 20 and longitudinal member 100. Crown 60 includes a first end 61 that faces towards the screw 20, and a second end 62 that faces towards the longitudinal member 100. A shelf 63 is formed on the exterior between the ends 61, 62, and a neck 65 extends upward beyond the shelf 63. An opening 66 with a width x1 extends through the crown 60 to provide access to the driving feature 22 on the screw 20. When the crown 60 is positioned within the receiver 30, the shelf 63 contacts against the ledge 36, with the neck 65 extending within the upper constriction 40 formed by the ledge 36. An inner surface 64 of the crown 60 may be curved to accommodate the spherical head 21. In one embodiment, the curve of the inner surface 64 matches the curve of the head 21 to facilitate pivoting movement of the screw 20. In other embodiments, the curve of the inner surface 64 may be greater than or less than the curve of the head 21.

Figure 4:
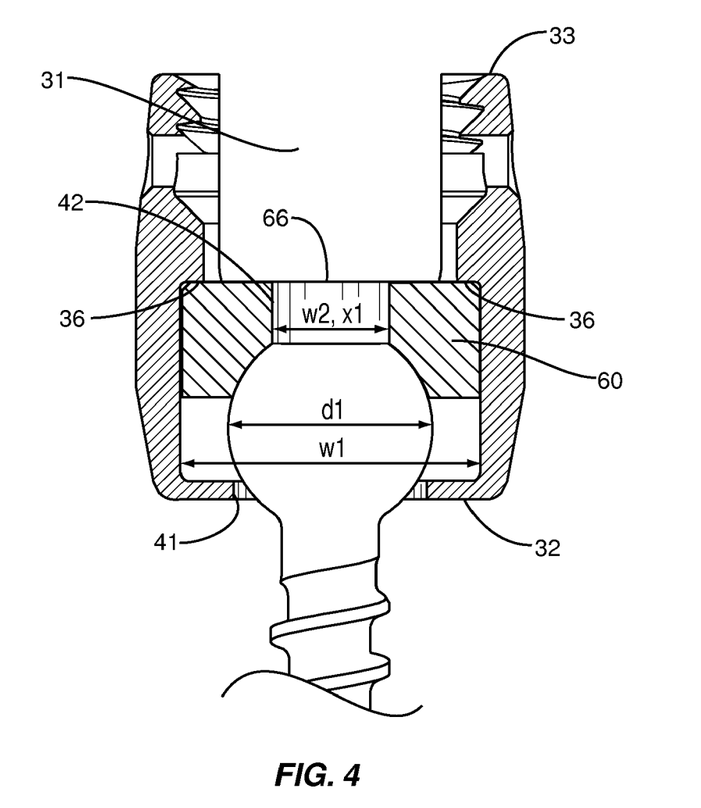
FIG. 4 is a section view of a receiver with a screw according to one embodiment.

In one embodiment as illustrated in FIG. 4, the upper constriction 40 is formed by the crown 60. Receiver 30 includes a ledge 36 sized to receive the crown 60. The space formed between the ledge 36 includes a width that is greater than the width d1 of the head 21. Crown 60 is positioned within this space and extends inward from the sidewalls 35 and ledge 36. Crown 60 includes an opening 66 including a width x1 that is smaller than the width d1 of the head 21. Crown 60 thereby forms the upper constriction 40 that prevents the screw 20 from moving vertically upward within the receiver 30. Because the crown 60 forms the upper constriction 40, the opening width x1 is the width of the upper constriction w2.

The receiver 30 is deformable to form a lower constriction 41 and capture the screw 20. The receiver 30 is deformed from a first orientation with the chamber 34 sized to receive the screw head 21, and a second orientation that captures the screw 20. The deformation provides for loading the screw head 21 into the chamber 34 through the first end 32 while the receiver 30 is in the first orientation. Once the screw head 21 is in the chamber 34, the receiver 30 is deformed to the second orientation to capture the screw head 21.

Figure 5:
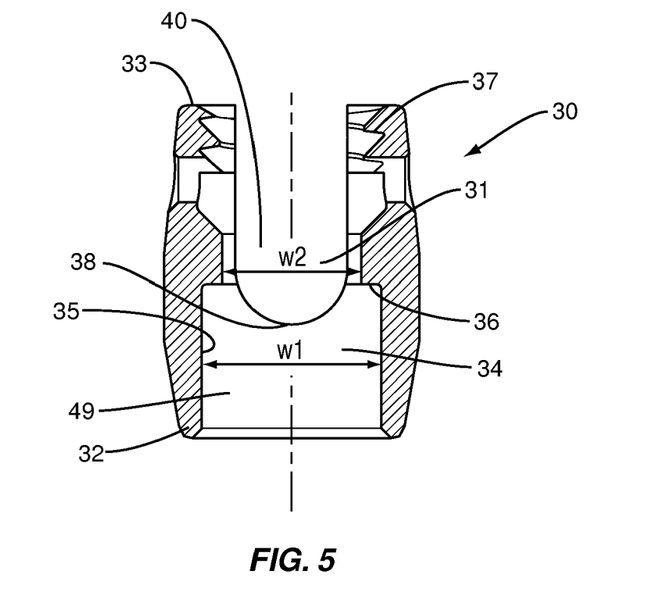
FIG. 5 is a section view of a receiver according to one embodiment.
Figure 7:
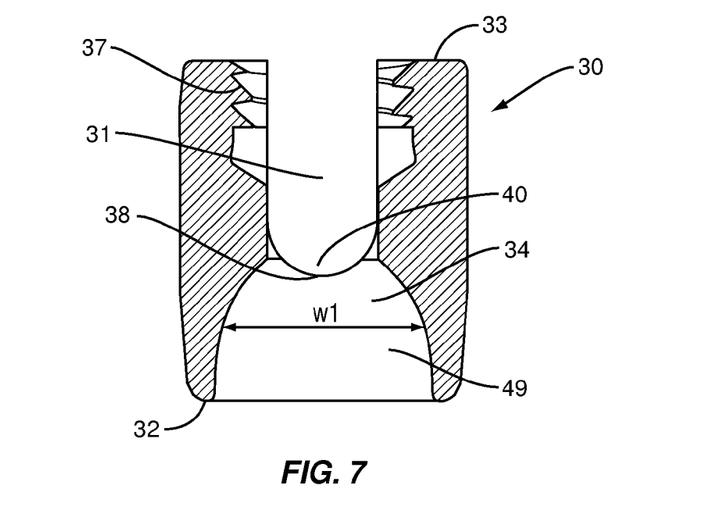
FIG. 7 is a section view of a receiver according to one embodiment.

FIG. 5 illustrates one embodiment with the receiver 30 in the first, un-deformed orientation. The chamber 34 includes a width w1 sized to receive the screw head 21 when it is inserted through the first end 32. In this embodiment, width w1 is substantially equal throughout the levels of the chamber 34. FIG. 6 illustrates another embodiment of the receiver 30 in the first orientation with the first end 32 including a smaller width than an interior width w1 of the chamber 34. The width of the first end 32 is larger than width d1 to receive the screw head 21 and allow it to pass into the central section 49 of the chamber 34. FIG. 7 illustrates an embodiment with the width of the first end 32 being larger than the width w1 of the central section 49.

The width of the screw head 21 may be substantially equal to the width w1 as illustrated in FIG. 3. In another embodiment, the width of the screw head 21 is less than the width w1 which allows for the screw head 21 to laterally move within the chamber 34.

Deformation forms a lower constriction 41 to capture the screw head 21 within the chamber 34. The deformation deforms the section inward towards a centerline C of the assembly 10. The lower constriction 41 includes a width w3 that is smaller than the head width d1. This is clearly shown in FIG. 3 with the first end 32 deformed inwards to form the lower constriction 41 that is smaller than the width d1 to prevent the head 21 from escaping from the chamber 34.

Figure 8A:
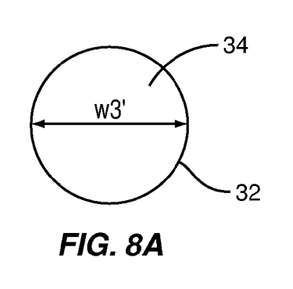
FIG. 8A is a schematic bottom view of a first end of a receiver in a first orientation according to one embodiment.
Figure 8B:
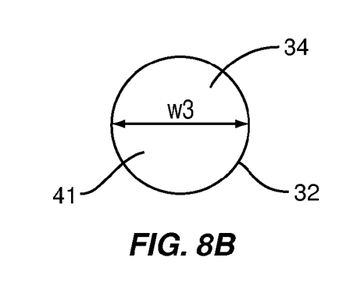
FIG. 8B is a schematic bottom view of a first end of a receiver in a second orientation according to one embodiment.

FIGS. 8A and 8B illustrate schematic bottom views of the receiver 30. For purposes of clarity, the screw 20 is not illustrated in either of the Figures. The first end 32 of the receiver 30 forms a continuous wall that encloses the chamber 34. FIG. 8A illustrates the receiver 30 in the first orientation with a width w3' formed at the first end 32. Width w3' is greater than or equal to the width d1 of the head 21 to allow insertion of the head 21 into the chamber 34. Because of the relative sizes, the first end 32 does not expand due to insertion of the head 21. FIG. 8B illustrates the receiver 30 in the second orientation with the first end 32 being deformed to a smaller width w3 thus forming the lower constriction 41 to retain the head 21. In one embodiment, the head 21 includes a greater width than the first end 32. Insertion of the head 21 causes either deformation of the head 21 or deformation of the receiver 20 to allow for insertion.

Figure 9:
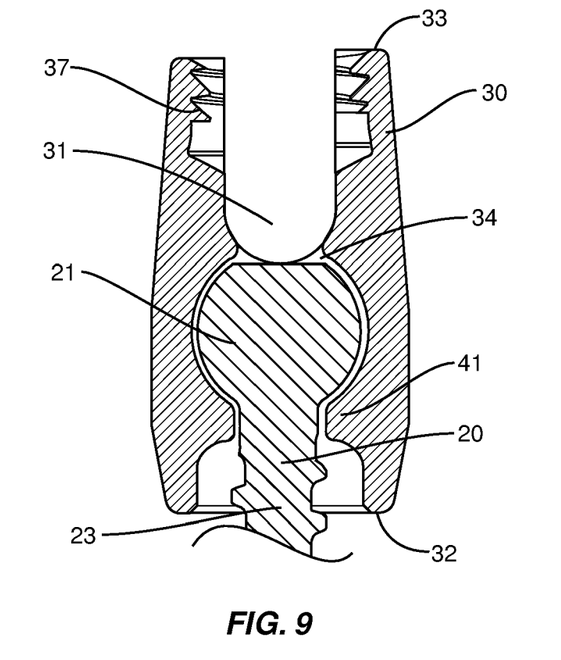
FIG. 9 is a section view of an screw and a receiver according to one embodiment.

The lower constriction 41 may be formed at different levels along the chamber 34. As previously discussed above, FIG. 3 includes the lower constriction 41 formed at a lower level of the chamber 34 with deformation of the first end 32. FIG. 9 illustrates an embodiment with deformation occurring at an upper level with the lower constriction 41 spaced inward from the first end 32.

The lower constriction 41 further forms a seat that is contacted by the lower surface of the head 21 when the set screw 50 engages the longitudinal member 100. The lower constriction 41 may include a shape that complements the shape of the head 21. FIGS. 3 and 9 illustrate embodiments with the surface of the lower constriction 41 that faces the head 21 substantially matching the curvature of the head 21. FIG. 4 illustrates an embodiment with the surface of the lower constriction 41 including a non-matching head shape. In these embodiments, the surface of the lower constriction 41 is substantially flat with the head 21 being curved. In another embodiment, the seat is formed by a curved section that is intermediate between two elongated, flat sections.

Figure 10:
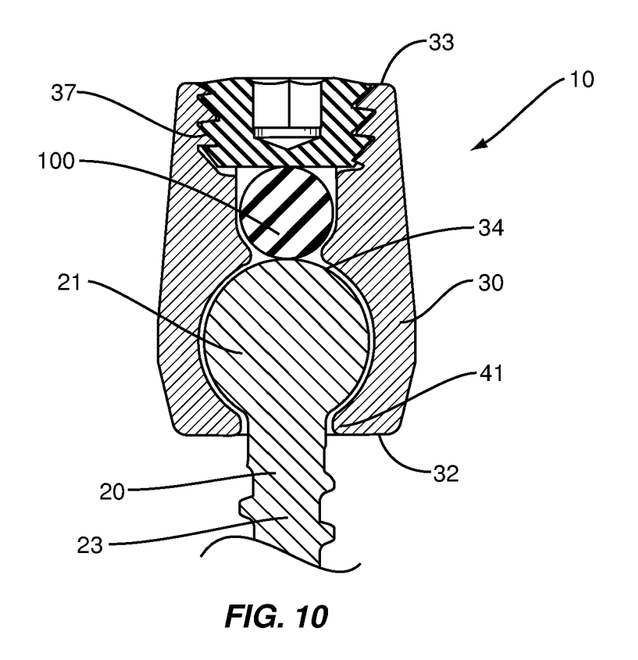
FIG. 10 is a section view of a multi-axial screw assembly with a longitudinal member according to one embodiment.

The size of the chamber 34 within the receiver 30 may vary. FIG. 3 illustrates the chamber 34 sized and positioned such that a portion of the head 21 extends outward beyond the first end 32 of the receiver 30. The height of the chamber 34 measured between the constrictions 40, 41 is such that the lower constriction 41 contacts an intermediate section of the head 21. In another embodiment as illustrated in FIGS. 9 and 10, the head 21 is contained above the lower constriction 41 with the shank 23 extending outward beyond the opening in the lower constriction 41.

Deformation of the receiver 30 may be performed using a variety of techniques. One technique is orbital forming which is a cold metal forming process during which the workpiece (the receiver 30 in this case) is captured between upper and lower dies. The process features one or the other of these dies orbiting relative to the other with a compression force applied therebetween. Due to this orbiting motion over the workpiece, the resultant localized forces can achieve a high degree of deformation at a relatively low compression force level.

Figure 11A:
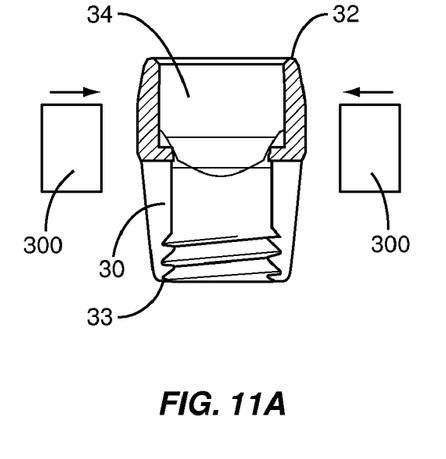
FIGS. 11A-11D are exemplary process steps of deforming the receiver according to one embodiment.
Figure 11B:
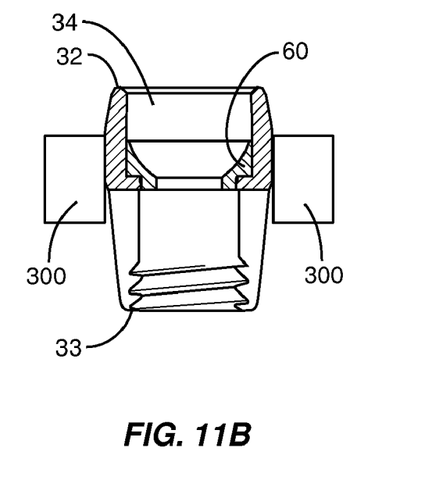

FIGS. 11A-11D depict exemplary process steps that may be used to retain the screw head 21 within the receiver chamber 34. To illustrate the process, the receiver 30 illustrated in FIG. 3 is shown. It should be understood that other receiver embodiments may be formed using the illustrated process steps. In a first step illustrated in FIG. 11A, the receiver 30 is positioned into a holding fixture 300. The fixture 300 is depicted as a pair of opposed jaws, but other types of fixtures, including a chuck, a vise, a clamp, or other device known in the art may be used. The fixture 300 is adjusted to a position as shown in FIG. 11B to secure the receiver 30. Once secured, the crown 60 is inserted into the chamber 34.

Figure 11C:
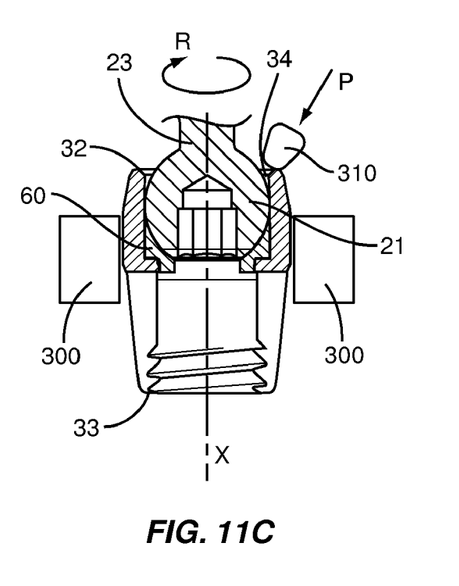
Figure 11D:
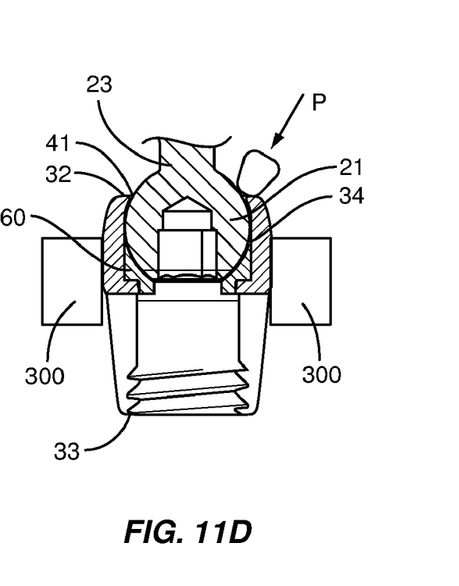

Next, the screw 20 is inserted into the receiver 30 with the head 21 being inserted through the first end 32 and into the chamber 34. Then, as FIG. 11C depicts, a forming tool 310 is brought into contact with the portion of the receiver 30 to be deformed. In the present example, the first end 32 is deformed under the influence of a deforming pressure P applied through the forming tool 310. The receiver 30, the forming tool 310, or some combination thereof may be rotated while the deforming pressure P is applied to the first end 32. The tool 310 is held at a fixed angle and progressively deforms the receiver 30 to the second orientation. The first end 32 is thereby deformed to the position shown in FIG. 11D with the first end 32 forming a lower restriction 40 to retain the head 21 within the chamber 34. The shape of the forming tool 310 may vary depending upon the desired shape of the deformed receiver 30. Orbital forming may also be referred to as spinning, radial riveting, bracketing, spin riveting, peening, or noiseless riveting.

Figure 12:
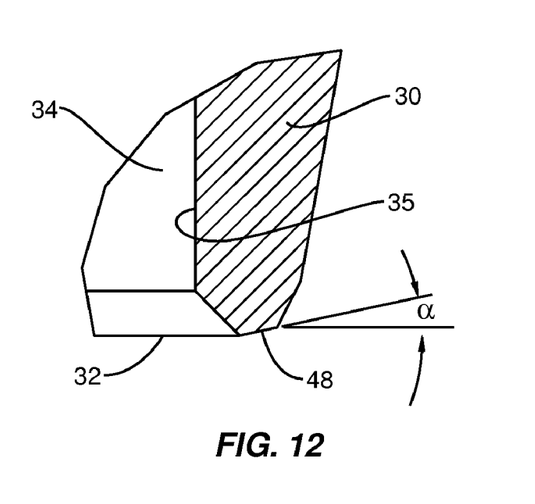
FIG. 12 is a partial section view of a first end of a receiver according to one embodiment.

FIG. 12 illustrates one embodiment of the receiver 30 with an exterior contact surface 48. When the receiver 30 is mounted within the fixture 300, the contact surface 48 is initially contacted by the forming tool 310 as illustrated in FIG. 11C. The contact surface 48 is positioned at an angle α relative to the first end 32. This position provides for good contact between the receiver 30 and the forming tool 310 during the deformation. In one embodiment, the angle α is about 12°.

Another deformation process includes a stamping/forming process. This process includes a die that holds the receiver 30 while the head 21 is inserted within the chamber 34. A punch applies a force to the receiver 30 to deform the receiver 30 towards the second orientation. This process may include a single step to deform the receiver 30 from the first orientation to the second orientation, or may include a series of progressive steps that use different tools or operations to obtain the final form. The steps may include crimping or rolling operations to compress edges and add rigidity to the receiver 30.

Roller forming is another process that may be used to deform the receiver 30. Roller forming uses multiple rollers mounted on a rotating spindle. Relative rotation between the receiver and the spindle cause the rollers to gradually and smoothly deform the receiver 30 thereby forming the lower constriction 41.

Spinning is another process for deforming the receiver 30. Spinning includes mounting the receiver 30 on a lathe. A tool, often referred to as a spoon, contacts the receiver 30 and applies a levered force. The receiver 30 is thereby deformed and shaped over a mandrel or form.

Magnetic forming may also be used to deform the receiver 30. This process includes application of an electric current near the receiver 30 that generates a pulsed magnetic field. The field creates a controllable pressure that can be applied to deform the receiver 30 as necessary.

The processes described above include exemplary methods to deform the receiver 30. It should be understood that other known manufacturing processes may be used to deform the receiver 30 to retain the screw 20. Some exemplary processes that may be used to achieve the desired deformation may include pressing, rolling, welding, spin forming, heading, forging, swaging, staking, and stamping. Those skilled in the art will comprehend other manufacturing techniques that may be used to effectively capture the screw 20 as desired.

Embodiments including a crown 60 originally allow for the screw 20 to be movable between various angular positions. The set screw 50 engages the receiver 30 and applies a compression force to the longitudinal member 100. This force is transferred through the crown 60 to the head 21 to secure the screw 20 at a desired angular position.

FIG. 10 includes an embodiment without a crown 60 and the longitudinal member 100 directly contacting the head 21. The compression force applied by the set screw to the longitudinal member 100 is transferred to the head to lock the screw 20 at the desired angular position.

Figure 13:
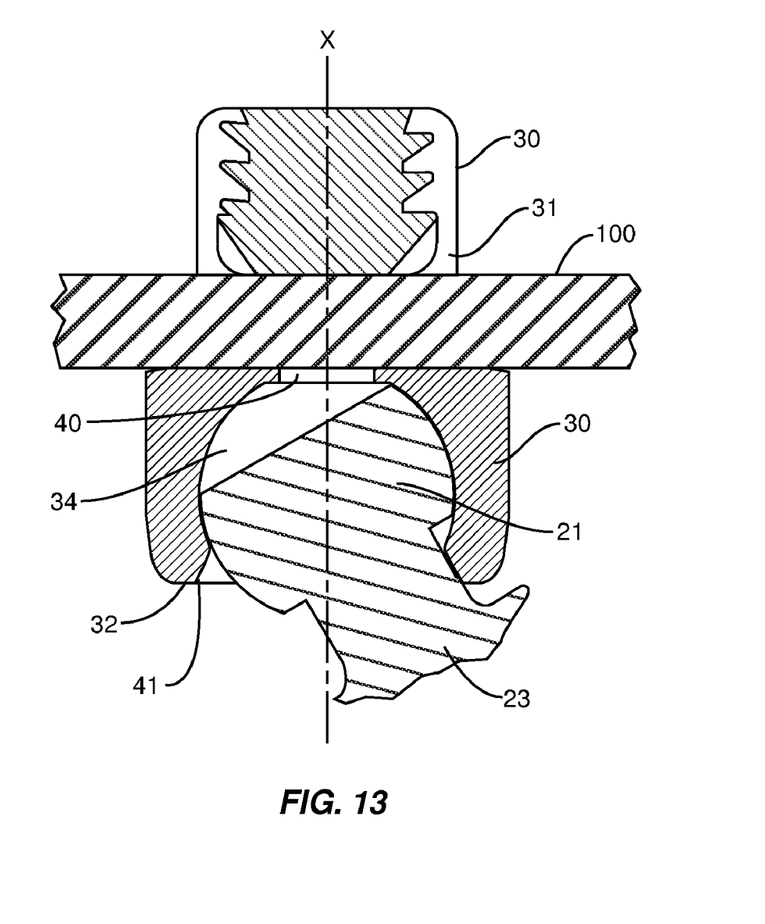
FIG. 13 is a section view of a multi-axial screw assembly and a longitudinal member according to one embodiment.

FIG. 13 illustrates an embodiment with the chamber 34 including an upper constriction 40 and a lower constriction 41 to capture the screw head 21. The head 21 is positioned away from the longitudinal member 100 when the set screw 50 is engaged with the receiver 30 and in contact with the longitudinal member 100. This provides for the screw 20 to remain movable relative to the receiver 30 once the longitudinal member 100 is secured by the set screw 50.

Figure 14:
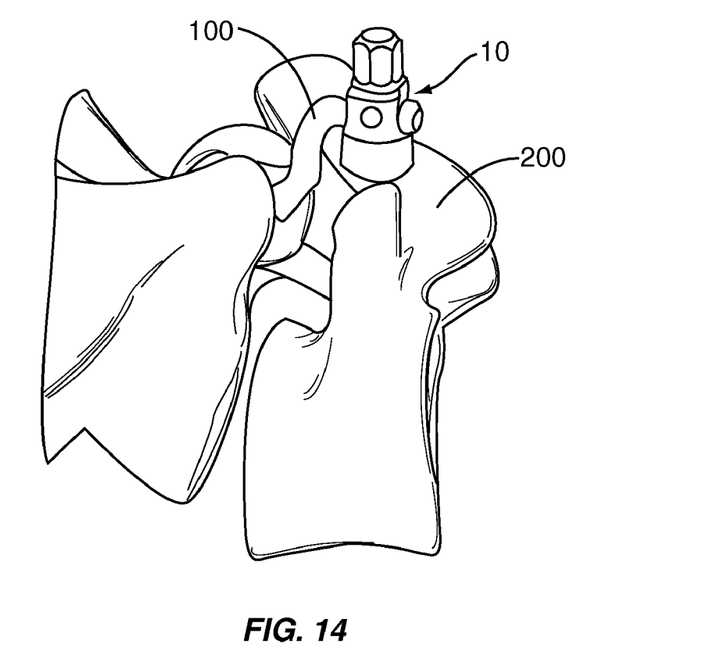
FIG. 14 is a perspective view of a multi-axial screw assembly and a longitudinal member according to one embodiment.

Various types of longitudinal members 100 may be used for spinal applications. In one embodiment, the longitudinal member 100 includes an elongated shape to extend across two or more vertebral members 100. FIG. 14 illustrates another type of longitudinal member 100 that is secured between vertebral members 200. In the specific embodiment of FIG. 14, the longitudinal member 100 extends between the sacrum and L5. Longitudinal members 100 may be flexible and constructed from various materials including a resin or polymer compound. Some flexible non-metallic longitudinal members 100 are constructed from materials such as PEEK and UHMWPE. Other types of flexible longitudinal members 100 may comprise braided metallic structures. In one embodiment, the longitudinal member 100 is rigid or semi-rigid and may be constructed from metals, including for example stainless steels, cobalt-chrome, titanium, and shape memory alloys. Further, the longitudinal member 100 may be straight, curved, or comprise one or more curved portions along its length.

Figure 15:
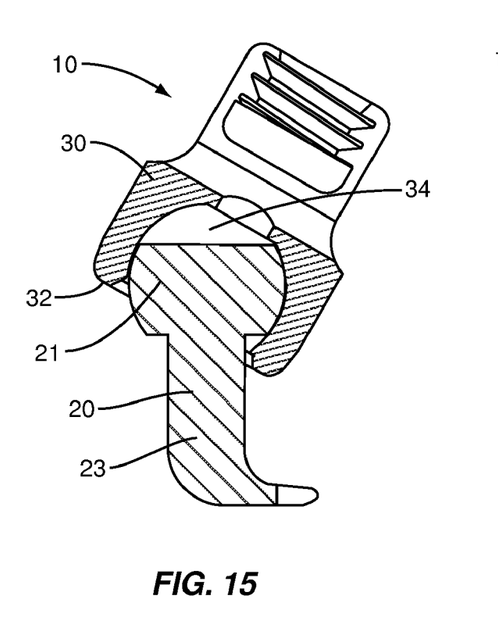
FIG. 15 is a section view of a multi-axial screw assembly according to one embodiment.
Figure 16:
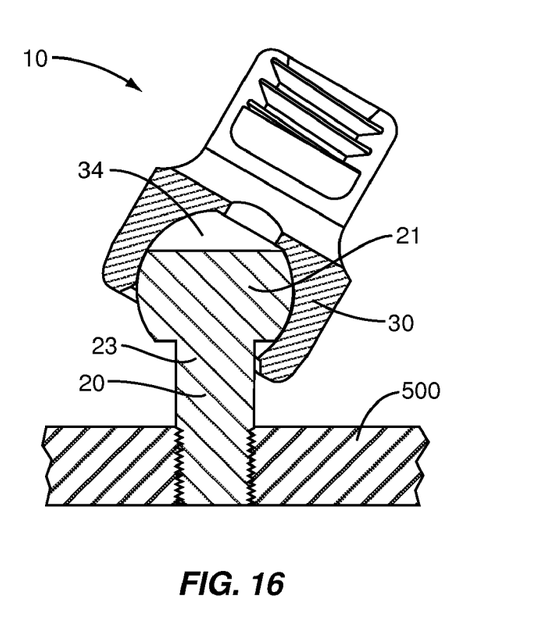
FIG. 16 is a perspective view of a multi-axial screw assembly according to one embodiment.

In one embodiment as illustrated in FIGS. 2 and 3, the head 21 is substantially spherical to allow multi-axial pivoting of the screw 20 relative to the receiver 30. In other embodiments, the screw head 21 has other shapes to allow motion in fewer directions. For instance, a disc-shaped screw head 21 may provide motion within a desired plane. Head 21 may also include a substantially flat surface as illustrated in FIGS. 15 and 16. Head 21 may also include friction enhancing features, such as a plurality of serrations, that are configured to engage the bearing surface of the crown 60 once a sufficient clamping force is applied onto the longitudinal member 100 and onto the crown 60, by the set screw 50.

Embodiments described above have contemplated a screw 20 that comprise threads for insertion into a vertebral member 200. Certainly, the multi-axial screw assembly 10 may include other types of screws 20. For example, FIG. 15 illustrates a screw 20 comprising a head 21 incorporated onto a hook-type screw member 20. In another embodiment shown in FIG. 16, the head 21 is incorporated onto a type of threaded screw member 20 that is inserted into a plate 500 instead of a bony member.

The longitudinal member 100 is captured within the receiver 30 by the set screw 50. Set screw 50 may include a shape to fit within the interior of the receiver 30 as illustrated in FIG. 3, or on the exterior as illustrated in FIG. 6. The longitudinal member 100 may also be captured by other structures, including but not limited to a twist lock and bayonet-type structure.

The longitudinal member 100 may move relative to the vertebral members 200. This may occur when the patient moves, such as during flexion or extension. During movement of the longitudinal member 100, the screw assemblies 10 remain attached at fixed locations to the longitudinal member 100. In one embodiment, the set screws 50 securely attach the receivers 30 to the longitudinal member 100. In one embodiment, one or more of the receivers 30 may translate along the longitudinal member 100.

In one embodiment, the movement of the longitudinal member 100 may cause the receivers 30 to move relative to the screws 20. The extent of movement between the receivers 30 and the screws 20 may vary depending upon the amount of vertebral member movement, and the specific mechanics of the screw assemblies 10. In embodiments with multiple screw assemblies 10 attached to the longitudinal member 100, each of the assemblies may move the same or different amounts.

In one embodiment, the longitudinal member 100 is attached to the vertebral members 200 with at least two assemblies 10. The longitudinal member 100 is movable between a first configuration with a first linear distance between the first and second assemblies 10, and a second configuration with a second different linear distance between the first and second assemblies 10. During the movement, the receivers 30 remain longitudinally fixed relative to the longitudinal member and movable relative to the screws 20. In one embodiment, the longitudinal member 100 is constructed from an elastic material that may allow an increase in the distance during a first type of motion. The elastic material may also apply a force to the vertebral members 200 to return the longitudinal member 100 back towards the default, or original position. In another embodiment, the longitudinal member 100 may include a bend or curved section between the assemblies 10 that may become elongated during movement.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A multi-axial screw assembly to connect a longitudinal member to a vertebral member, the multi-axial screw assembly comprising:
   a screw comprising a threaded shank and an enlarged head; and
   a unitary body comprising an upper channel sized to receive the longitudinal member, a lower chamber to receive the head and being in communication with the upper channel, an upper constriction, and a lower constriction;
   both the upper and lower constrictions being narrower than the head and disposed on generally opposite sides of the lower chamber, the upper channel including a threaded section;
   the head being wider than the threaded section when the head is positioned in the lower chamber;
   the screw extending into the lower chamber through the lower constriction;
   the lower constriction 360° bounded by continuous material of said body.

2. The multi-axial screw assembly of claim 1, wherein the multi-axial screw assembly comprises a first state wherein the screw is selectively angularly positionable relative to the body and a second state wherein the screw is angularly locked relative to the body.

3. The multi-axial screw assembly of claim 1, wherein the chamber is sized such that a portion of the head extends outward from the chamber and beyond the body.

4. The multi-axial screw assembly of claim 1, wherein the lower constriction is spaced inward in the body and away from a lower end of the body.

5. The multi-axial screw assembly of claim 1, wherein the lower constriction is positioned at a lower end of the body.

6. The multi-axial screw assembly of claim 1, further comprising a crown positioned within the body, the crown including a first end with an inner surface that contacts the head and a second end that contacts the longitudinal member when the multi-axial screw assembly is in a locked, second state.

7. The multi-axial screw assembly of claim 6, wherein the crown further comprises a flange that contacts against a ledge in the lower chamber, the ledge including a smaller width than the lower chamber.

8. The multi-axial screw assembly of claim 1, wherein the lower constriction includes a circular shape.

9. The multi-axial screw assembly of claim 1, further comprising a contact surface proximate to a lower end of the body, the contact surface being positioned at an angle of about 12° relative to the lower end.

10. The multi-axial screw assembly of claim 1, wherein at a vertical level of the lower chamber between the upper and lower constrictions, the body defining an outer extent of the multi-axial screw assembly and an inner wall of the lower chamber.

11. A multi-axial screw assembly to connect a longitudinal member to a vertebral member, the multi-axial screw assembly comprising:
a screw comprising a threaded shank and an enlarged head;
a unitary body comprising an upper channel sized to receive the longitudinal member, and a lower chamber to receive the head of the screw, the upper channel and the lower chamber being in communication; and
the lower chamber comprising a first constriction narrower than the head and positioned on an upper vertical side of the chamber, a second constriction narrower than the head and positioned on a lower vertical side of the chamber, and a central section located between the first and second constrictions and including an enlarged width greater than either the first and second constrictions;
the head disposed in the central section;
the upper channel including a threaded section that is narrower than the head of the screw when the head is positioned in the central section;
at a vertical level of the central section, the body defining an outer extent of the multiaxial screw assembly and an inner wall of the lower chamber.

12. The multi-axial screw assembly of claim 11, wherein the body is circumferentially un-reinforced at the vertical level of the central section.

13. The multi-axial screw assembly of claim 11, further comprising a crown that includes a neck that extends through the second constriction and a contact surface with a spherical surface that contacts the head.

14. The multi-axial screw assembly of claim 11, wherein the lower constriction is continuous and forms a 360° boundary around the screw.

* * * * *